United States Patent
Suga et al.

(10) Patent No.: US 8,102,522 B2
(45) Date of Patent: Jan. 24, 2012

(54) INSPECTION APPARATUS AND INSPECTION METHOD

(75) Inventors: Tadashi Suga, Tsukuba (JP); Shuichi Chikamatsu, Hitachinaka (JP); Masayuki Ochi, Hitachinaka (JP); Takahiko Suzuki, Hitachinaka (JP); Seiji Otani, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 541 days.

(21) Appl. No.: 11/989,018

(22) PCT Filed: Jun. 29, 2007

(86) PCT No.: PCT/JP2007/063126
§ 371 (c)(1),
(2), (4) Date: Jan. 18, 2008

(87) PCT Pub. No.: WO2008/001891
PCT Pub. Date: Jan. 3, 2008

(65) Prior Publication Data
US 2009/0262339 A1    Oct. 22, 2009

(30) Foreign Application Priority Data

Jun. 30, 2006  (JP) .................................. 2006-180638
Mar. 30, 2007  (JP) .................................. 2007-092779

(51) Int. Cl.
G01N 21/00    (2006.01)
(52) U.S. Cl. ................ 356/237.4; 356/237.2; 356/237.3
(58) Field of Classification Search .................... None
See application file for complete search history.

(56) References Cited

U.S. PATENT DOCUMENTS 6,721,047 B2    4/2004  Shimoda et al.

FOREIGN PATENT DOCUMENTS

| JP | 62-89336 | 4/1987 |
|---|---|---|
| JP | 1-117024 | 5/1989 |
| JP | 1-250847 | 10/1989 |
| JP | 6-258239 | 9/1994 |

(Continued)

OTHER PUBLICATIONS

English Translation of Previously submitted International Search Report issued in PCT/JP2007/063126 dated on Oct. 2, 2007.

(Continued)

*Primary Examiner* — Gregory J Toatley
*Assistant Examiner* — Amanda Merlino
(74) *Attorney, Agent, or Firm* — McDermott Will & Emery LLP

(57) ABSTRACT

A defect inspection apparatus enable to efficiently perform a temperature control without involving an enlarged size can be achieved.

The parts constituting the defect inspection apparatus are classified into parts need temperature control and parts not to need temperature control; all the parts need temperature control are accommodated together into a temperature-controlled part accommodating section 604, and the parts not to need temperature control are arranged in a heat radiating unit 605. The temperature in the temperature-controlled part accommodating section 604 is measured by a temperature measuring instrument 603 and a control CPU 602 in a temperature control unit 601 carries out control according to the measured temperature so that the interior of the temperature-controlled part accommodating section 604 is kept at a fixed temperature. Therefore, it becomes easy to keep the fixed temperature, when compared with a case in which individual parts are temperature-controlled separately by being heated or cooled, yielding an energy saving effect.

11 Claims, 16 Drawing Sheets

FOREIGN PATENT DOCUMENTS

| | | |
|---|---|---|
| JP | 6-324003 | 11/1994 |
| JP | 8-210989 | 8/1996 |
| JP | 8-271437 | 10/1996 |
| JP | 9-509247 | 9/1997 |
| JP | 11-344447 | 12/1999 |
| JP | 2000-105203 | 4/2000 |
| JP | 2002-90311 | 3/2002 |
| JP | 2004-157444 | 6/2004 |
| JP | 2005-77468 | 3/2005 |
| WO | WO 94/28397 | 12/1994 |

OTHER PUBLICATIONS

International Preliminary Report on Patentability and Written Opinion of the International Searching Authority, issued in corresponding International Patent Application No. PCT/JP2007/063126, mailed Jan. 29, 2009.

Japanese Office Action, with English translation thereof, issued in Japanese Patent Application No. 2007-092779 dated Feb. 1, 2011.

INSPECTION APPARATUS AND INSPECTION METHOD

RELATED APPLICATIONS

This application is the U.S. National Phase under 35 U.S.C. §371 of International Application No. PCT/JP2007/063126, filed on Jun. 29, 2007, which in turn claims the benefit of Japanese Application No. 2006-180638, filed on Jun. 30, 2006, and Japanese Application No. 2007-092779, filed on Mar. 30, 2007, and the disclosures of which Applications are incorporated by reference herein.

TECHNICAL FIELD

The present invention relates to an inspection apparatus and an inspection method. The present invention is suitable, for example, to a defect inspecting apparatus for checking for the presence of minute foreign matter and other types of defects by using an optical system, such as a semiconductor inspecting apparatus, as well as a defect inspection method.

BACKGROUND ART

As semiconductor circuits are becoming increasingly fine, minute foreign matter on semiconductor substrates becomes to affect the quality of semiconductor products.

As a technology for detecting this type of foreign matter on the semiconductor substrates, Patent Document 1 discloses an inspection apparatus and inspection method that improve detection sensitivity and a throughput by achieving high-efficiency linear illumination from a direction in which diffracted light is not delivered so as to reduce light diffracted from a pattern and by enabling thresholds to be set according to pattern-depending signal variations.

Patent Document 2 discloses an inspection apparatus that comprises a unit for storing the relation between temperatures measured in advance or calculated through simulation and focused point offsets, a unit for predicting a focused point offset from this relation between temperatures and focused point offsets according to a temperature detection result obtained by a temperature detecting unit, and a unit for correcting a focused point offset according to the prediction provided by that unit.

Patent Document 1: Japanese Patent Application Laid-open Publication No. 2000-105203

Patent Document 2: Japanese Patent Application Laid-open Publication No. 2002-090311

DISCLOSURE OF THE INVENTION

In the prior art, however, there is no consideration for a case in which the relation between actual variations due to temperatures and focused point offsets is not constant.

For example, it is apparent that different members used in a defect inspection apparatus respond to a change in temperature at different speeds and causes different amounts of variations. Accordingly, the amount of variations, that are its comprehensive result, varies as the temperature changes with time.

The time elapsed after the temperature changes may be minute or sufficient, however, the difference between the amount of variations, which are a comprehensive result, and an amount of prediction is within the depth of focus of an optical inspection system, the sensitivity of the inspection apparatus drops only a little.

If the amount of variations, which are a comprehensive result, is greater than the depth of focus of the inspection optical system with the amount of prediction considered or if the amount of variations is small at present but the depth of focus, which is given by "$z=\pm\lambda/2NA^2$" may become small due to technological innovation in the future, the drop of the inspection sensitivity of the apparatus for temperature changes can be no longer neglected.

To prevent this drop of the inspection sensitivity, it is necessary to suppress the amount of variations, which is a comprehensive result.

The use of a low thermal expansion material can be considered as a unit for suppressing the amount of variations caused by temperature changes, and temperature control can be considered as a unit for suppressing temperature changes.

However, the former unit is problematic in that the weight of the inspection apparatus is significantly increased, increasing burdens on the apparatus manufacturing line and a semiconductor line.

As an example of the latter unit, temperature control technology has been developed to maintain high precision in wafer overlaying positioning and the ease of imaging.

Specifically, an entire exposing apparatus is covered with a temperature control chamber, and temperatures of a measuring optical path space, a stage, structural supporting bodies, a lens, and a structural supporting body of the lens are controlled by individual chambers.

However, differences in positional precision demanded for targets, differences in optical structures, and different thermal sources make it difficult to apply the above temperature control technology to a defect inspection apparatus without alternation.

For example, the use of a temperature control chamber that covers an entire inspection apparatus enlarges the apparatus, resulting in large footprints. Therefore, burdens on the apparatus manufacturing line and semiconductor line are increased.

Technology that can efficiently control temperature while preventing the inspection apparatus from being enlarged is necessary.

An object of the present invention is to provide a defect inspection apparatus and a defect inspection method that can efficiently control temperature without involving an enlarged size.

In a defect inspection apparatus and a defect inspection method according to the present invention that emit light to a test object and detect reflected or scattered light to check for a defect in the test object, a plurality of parts that need temperature control are selected from a plurality of parts in the defect inspection apparatus and placed in a temperature-controlled part accommodating section, the temperature in the temperature-controlled part accommodating section is measured, and a temperature control unit performs temperature control so that the interior of the temperature-controlled part accommodating section is kept at a prescribed temperature.

According to the present invention, a defect inspection apparatus and a defect inspection method that can efficiently perform temperature control without involving an enlarged size can be achieved.

BRIEF DESCRIPTION OF DRAWINGS

FIG. 15 is a graph to indicate a focus error in compensation for temperatures.

FIG. 19 is a graph to indicate a focus error in compensation for atmospheric pressures.

LEGEND

Figure 1:
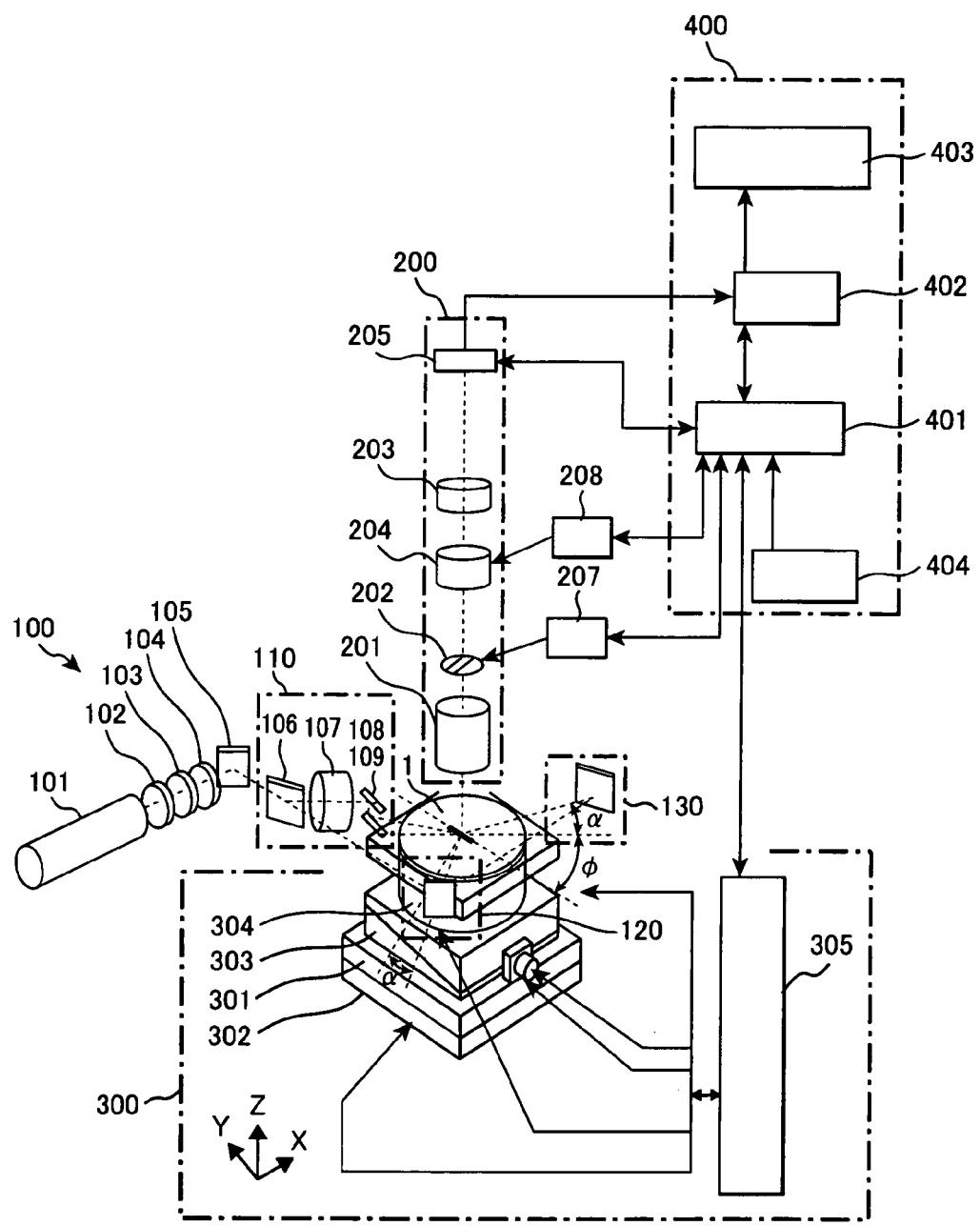
FIG. 1 is a drawing to show an entire structure of the defect inspection apparatus of the first embodiment in the present invention.

1: substrate under inspection (wafer), 2: chip, 3: slit beam, 4: area detected by an image sensor such as a TDI sensor, 100: illumination optical system, 101: laser light source, 102: concave lens, 103: convex lens, 104: optical filter group, 105: mirror, 106: optical branching element (direction 11), 107: illumination lens, 108: incident mirror, 109: angle-of-elevation switching mirror, 110: direction-11 lighting fixture, 114: optical branching element (direction 12), 115: optical branching element (direction 12), 120: direction-12 lighting fixture, 130: direction-13 lighting fixture, 200: inspection optical system, 201: objective lens, 202: Fourier transform face, 203: imaging lens, 204: varifocal lens group, 205: detector, 206: sensor Z driving mechanism, 207: spatial filter control unit, 208: lens driving control unit, 209: detected field, 210: auto focus unit, 300: stage unit, 301: X stage, 302: Y stage, 303: Z stage, 304: angle stage, 305: stage controller, 400: control system, 401: driving processing system, 402: image processing system, 403: display system, 404: input system, 500: base, 501: stone surface plate, 502: optical surface plate, 503: second optical surface plate, 600: temperature control system, 601: temperature control unit, 602: control CPU in the temperature control unit, 603: temperature measuring instrument, 604: temperature-controlled part accommodating section, 605: heat radiating unit, 611: outward pipe of the temperature control medium, 612: inward pipe of the temperature control medium, 613: flow path in the main body of the temperature control unit, 614: clean filter, 615: fan filter unit (FFU), 616: airflow (of clean air), 617a, 617b: heat insulating valve, 1500: focus detection optical system, 1501: focus detection light source, 1502: focus detection phototransmitting optical system, 503: photoreceiving optical system, 1504: focus detection sensor, 1505: focus signal processing unit, 1600: atmospheric pressure and temperature sensor system, 1601: atmospheric pressure sensor, 1602: atmospheric pressure data logger, 1603: temperature sensor, 1604: temperature data logger

BEST MODE FOR CARRYING OUT THE INVENTION

Embodiments of the present invention will be described below with reference to the drawings.

First Embodiment

A defect inspection apparatus in a first embodiment of the present invention will be described with reference to FIGS. 1 to 7.

In the embodiment described below, a surface foreign matter inspection apparatus will be used as an example of the defect inspection apparatus.

The first embodiment of the present invention suppresses variations in focused positions through temperature control to ensure stable inspection sensitivity, reduces the number of times an apparatus has needed to stop on an apparatus manufacturing line or semiconductor line to calibrate inspection sensitivity due to variations in focused positions, achieves efficient heat exchange while reducing the price of the apparatus and footprints by devising an arrangement of the apparatus, and eliminates the use of a fan filter unit (FFU) by using temperature-controlled air as clean air.

FIG. 1 shows the entire structure of a defect inspection apparatus to which the present invention is applied. The defect inspection apparatus in the first embodiment, shown in FIG. 1, comprises a stage unit 300, an illumination optical system 100, at least one inspection optical system 200, a control system 400, and a temperature control system 600 (shown in FIG. 2).

The stage unit 300 has an X stage 301, a Y stage 302, a Z stage 303, an angle stage 304, and a stage controller 305. When a wafer 1 is placed on the stage unit 300, the angle stage 304 performs alignment in an angular direction and the Z stage 303 performs alignment in the Z direction.

When the wafer 1 is scanned, the X stage 301 performs scanning in the X direction, the Y stage 302 feeds the wafer 1 in the Y direction, and then the X stage 301 performs scanning in the reverse direction. This cycle is repeated.

Figure 5:
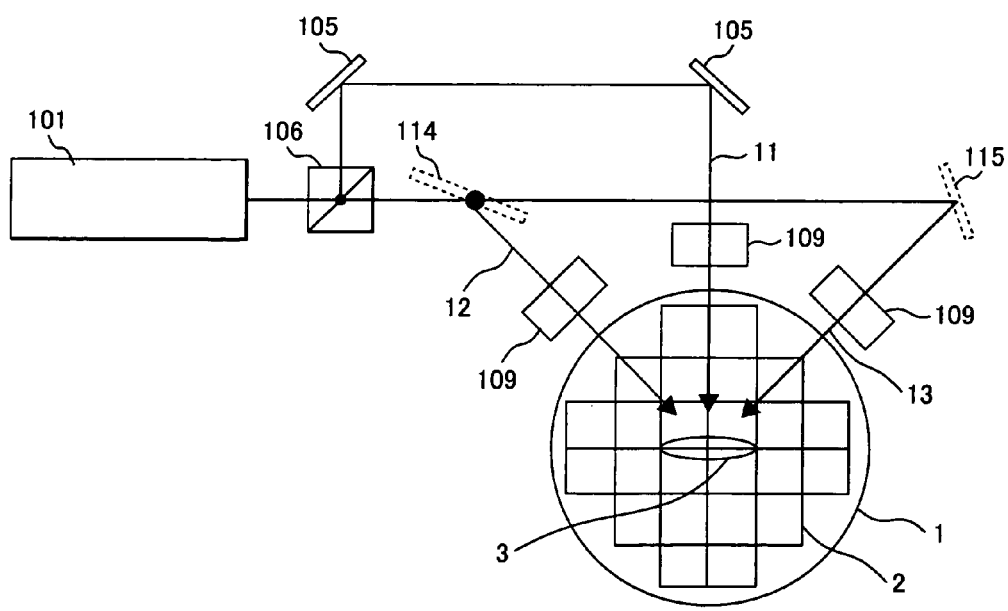
FIG. 5 is a top view of an illumination optical system.

The illumination optical system 100 has a common optical path and a plurality of illuminating unit, which are a lighting fixture 110 (first illuminating unit) in a direction 11 (shown in FIG. 5), a lighting fixture 120 (second illuminating unit) in a direction 12 (shown in FIG. 5), a lighting fixture 130 (third illuminating unit) in a direction 13 (shown in FIG. 5).

Parts in the common optical path include a laser light source 101, a concave lens 102 and convex lens 103 that fulfill the role of a beam expander, an optical filter group 104 including an ND filter and a wavelength plate, and a mirror 105 for routing an optical path.

The illumination optical system 100 has an optical branching element (or mirror) 106 that can be switched to a transparent glass plate as a part of a lighting fixture in each direction, an illumination lens 107, an incident mirror 108 for directing the optical path in the vertical direction, and angle-of-elevation switching mirrors 109.

The beam that has passed through the illumination lens 107 is directed as slit beams 3 from three directions 11, 12, and 13 on the wafer 1 so that its short-side direction matches the array direction of chips 2, as shown in FIG. 5.

To perform defect inspection at high speed, the slit beams 3 are directed so that the scanning direction X on the X stage 301 matches the short-side direction and the scanning direction Y on the Y stage 302 matches the long-side direction.

That is, when the amount of feed in the Y direction is increased, the total amount of scanning on the stages can be reduced.

The illumination intensity (power) of a beam light flux emitted from the laser light source 101 can be controlled by using the ND filter of the optical filter group 104 or the like.

The inspection optical system 200 comprises an objective lens 201, a Fourier transform face 202, which is controlled by a spatial filter control unit 207, an imaging lens 203, a varifocal lens group 204, which is controlled by a lens driving control unit 208, and a detector 205, such as a TDI sensor. The inspection optical system 200 first directs the slit illumination 3 to the wafer 1 and gathers generated light and scattered light with the objective lens 201.

An interfered part of diffracted light, which appears on the Fourier transform face 202 dominated by repeated patterns on the wafer 1, is then shielded by a spatial filter (not shown).

Light that has transmitted through the spatial filter undergoes magnification ratio adjustment by the varifocal lens group 204.

Finally, the imaging lens 203 forms an image on the detector 205. An area that concurrently satisfies a detected field 209 (shown in FIG. 4) on the wafer 1 and a detected area 4 (shown in FIG. 4) is focused on the sensor of the detector 205.

When the slit beams 3 are directed to the wafer 1 on which various forms of circuit patterns are formed, reflected and scattered lights are ejected from the circuit patterns and defects such as foreign matter on the wafer 1. Reflected and scattered lights generated from the circuit patterns are shielded by the spatial filter. Lights that have transmitted through the spatial filter are focused on the detector 205 and undergo photoelectric conversion.

The control system 400 comprises a driving control system 401 for controlling a driving mechanism and the sensor, an image processing system 402, a display system 403, and an input system 404.

The image processing system 402 comprises an A/D converter for data resulting from photoelectric conversion by the detector 205, a data memory, a difference processing circuit for obtaining a difference in signals between chips 2, a memory for tentatively storing a differential signal between chips 2, a threshold calculating part for setting a pattern threshold, a comparison circuit, and an inspection result storing system for storing and outputting defect detection results such as for foreign matter.

Figure 2:
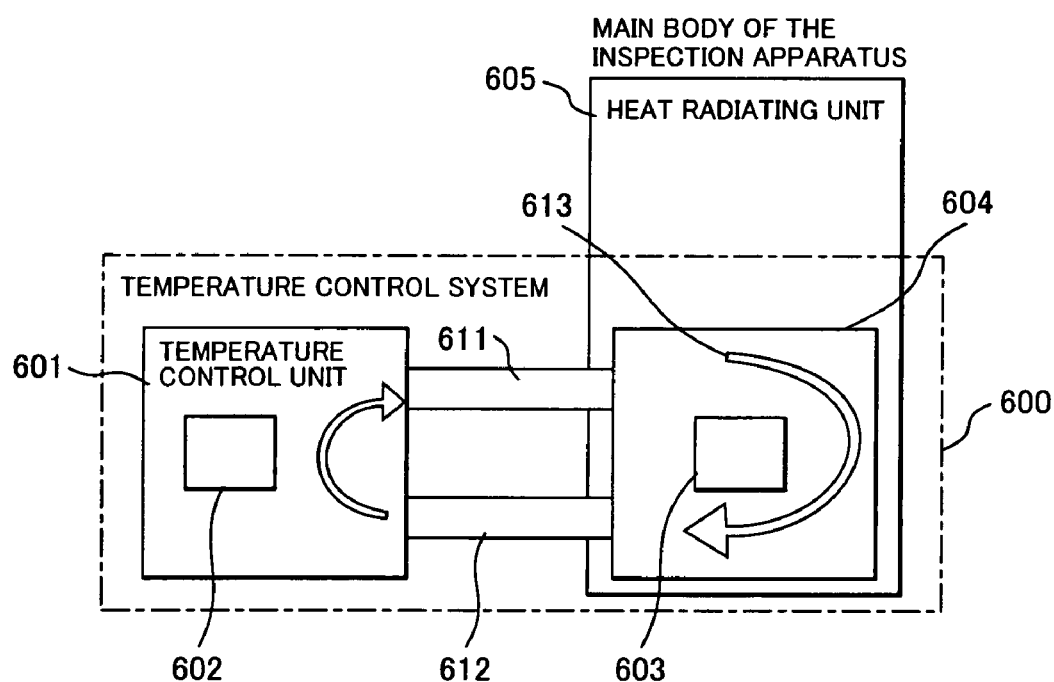
FIG. 2 is a drawing to illustrate the principle of the first embodiment of the present invention.
Figure 6:
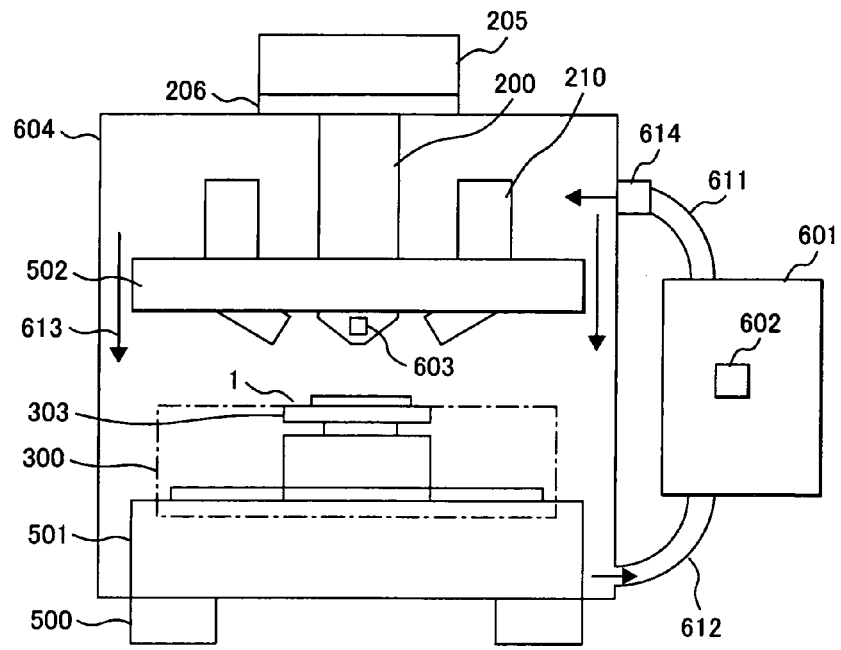
FIG. 6 is a structural drawing of a temperature control system in the first embodiment.

Furthermore, as shown in FIG. 6, units in the first embodiment of the present invention include an auto focus system 210 having optical paths provided separately from the objective lens 201 and inspection optical system 200, an optical surface plate 502 on which to mount the inspection optical system 200, auto focus system 210, and illumination optical system 100, and a stone surface plate 501 on which to mount the optical surface plate 502 and stage unit 300, and a temperature control system 600 (shown in FIG. 2).

FIG. 2 illustrates the principle of the first embodiment of the present invention. As shown in FIG. 2, the temperature control system 600 comprises a temperature control unit 601, a temperature measuring instrument 603 (first temperature measuring unit), an outward pipe 611 and an inward pipe 612 for supplying temperature-controlled airflow to the main body of the apparatus, and a temperature-controlled part accommodating section 604.

The temperature-controlled part accommodating section 604 occupies space between the lower end of the stone surface plate 501 and the lower end of a sensor Z driving mechanism 206; the inspection optical system 200 and auto focus system 210 are accommodated in the space.

Out of a plurality of parts in the defect inspection apparatus, the temperature-controlled part accommodating section 604 accommodates a plurality of parts that need temperature control. Parts that do not need temperature control are accommodated in a heat radiating unit 605.

That is, the parts constituting the defect inspection apparatus are classified into parts that need temperature control and parts that do not need temperature control; the parts that need temperature control are kept at a fixed temperature in a collective manner.

The heat radiating unit 605 in FIG. 2 accommodates at least the detector 205 and other parts that become heat sources, and may accommodate a driving part (not shown) of the stage unit 300, the laser light source 101, and the control system 400 and other parts that become heat sources.

Causes why the imaging position is shifted due to temperature changes are a first focal length change caused by a change in index of refraction on an optical path, a second focal length change caused by deformation of the cylinder of the objective lens 201, and a third focal length change caused by deformation of the optical surface plate 502 or stone surface plate 501 and a positional change of the auto focus unit 210 or objective lens 201 mounted on the optical surface plate 502 and stone surface plate 501.

In particular, the third focal length change varies at a start point and end point of the temperature change and during the duration of the change, because the causative parts comprise a plurality of members having different thermal time constants.

Accordingly, if the present invention is not applied, it is difficult to predict the amount of change and make compensation, so periodic calibration is needed to avoid unstable inspection sensitivity and the apparatus is forced to stop on the apparatus manufacturing line or semiconductor line each time calibration is performed.

In the first embodiment of the present invention, since the temperatures of the parts related to imaging position displacement (objective lens 201, auto focus unit 210, stone surface plate 501, and optical surface plate 502) are fixed, that is, these parts (objective lens 201, auto focus unit 210, stone surface plate 501, and optical surface plate 502) are accommodated in the temperature-controlled part accommodating section 604 and controlled so that their temperatures are fixed, focal length changes (imaging position displacement) that are difficult to predict can be eliminated and thereby inspection sensitivity can be made more stable.

Figure 7:
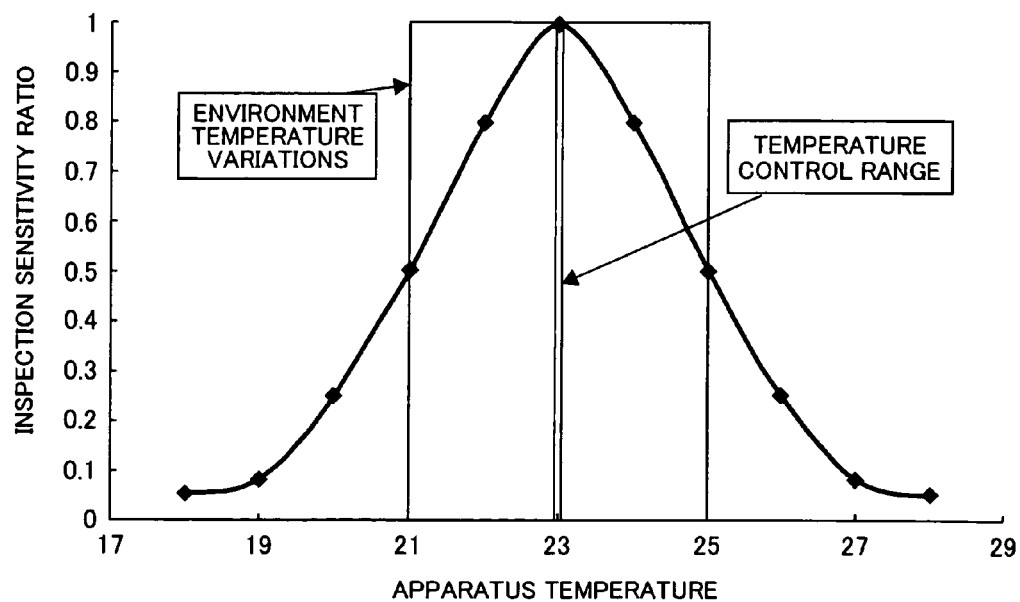
FIG. 7 is a graph to illustrate the inspection sensitivity stability achieved by temperature control according to the present invention.

If the apparatus temperature is controlled in the range around 23° C., for example, as shown in FIG. 7, the inspection sensitivity is stabilized, so the number of times the apparatus has to stop on the apparatus manufacturing line or semiconductor line due to inspection sensitivity calibration can be reduced.

In the first embodiment of the present invention, temperature-controlled clean air is supplied into the temperature-controlled part accommodating section 604 (in which a heat insulating material is used to prevent heat inflow from and heat outflow to the ambient space), as shown in FIGS. 2 and 6, so the interior of the defect inspection apparatus can be kept clean without a fan filter unit (FFU) being installed.

Dust generated in the apparatus flows along an airflow 613 of the clean air and is efficiently removed by a clean filter 614 (shown in FIG. 6).

To keep the interior of the defect inspection apparatus clean, the clean air preferably circulates in the temperature-controlled part accommodating section 604 and temperature control unit 601 in such a way that the clean air is supplied downwardly.

The clean filter 614 is preferably disposed at an intermediate point in the outward pipe 611 and immediately before the temperature-controlled part accommodating section 604.

This is because the degree of cleanness can be made highest as compared when the clean filter 614 is disposed in other places.

Incidentally, the clean air must flow in one direction, so the airflow cannot be circulated within the temperature-controlled part accommodating section 604.

A slight temperature gradient is generated along the airflow 613 in the temperature-controlled part accommodating section 604.

Here, a key point is that stable temperature around each target that needs temperature control rather than a uniform temperature distribution in the temperature-controlled part accommodating section 604.

When the temperature state including the temperature gradient in each target that needs temperature control is stabilized, the stability of the inspection sensitivity can be improved.

Figure 3:
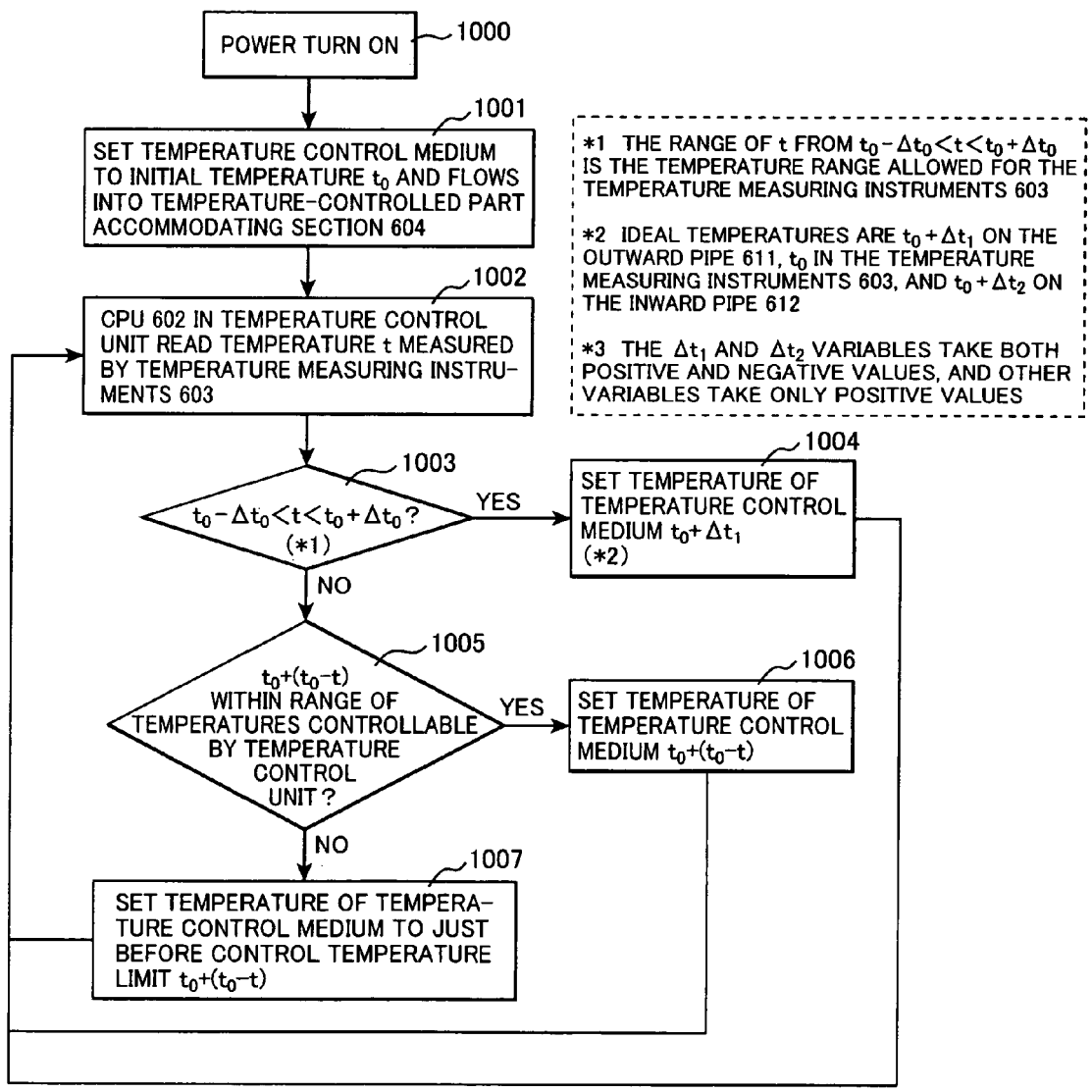
FIG. 3 is an operation flowchart for temperature control in the first embodiment of the present invention.
Figure 4:
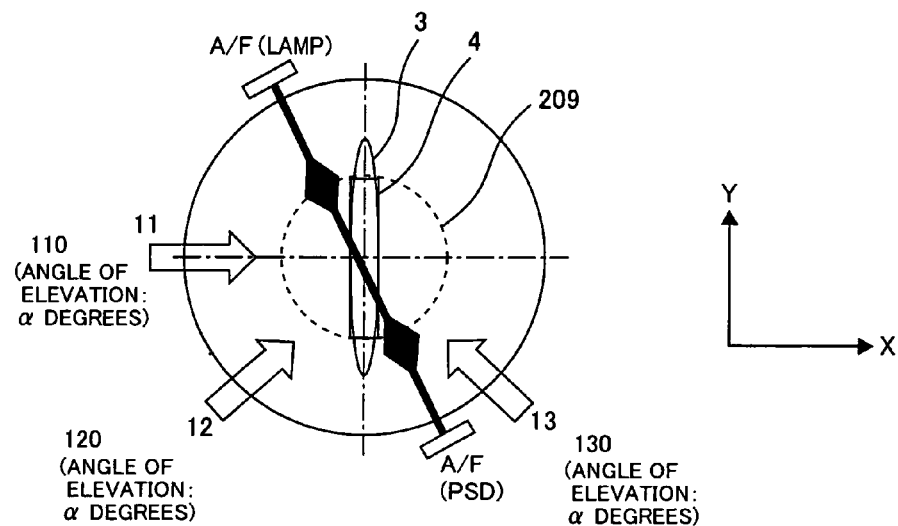
FIG. 4 is a drawing to illustrate an illumination to a sensor projecting surface on a substrate under inspection from three directions.

FIG. 3 is an operation flowchart for temperature control in the first embodiment of the present invention.

When power is turned on in step 1000 in FIG. 3, the temperature control system 600 sets a temperature control medium to initial temperature $t_0$ in step 1001 and flows the temperature control medium into the temperature-controlled part accommodating section 604.

In step 1002, temperature t in the temperature-controlled part accommodating section 604 is always monitored by the temperature measuring instruments 603, and obtained temperature data is loaded into a control CPU 602 in the temperature control unit through a communication cable.

To keep the temperature in the temperature-controlled part accommodating section 604 at a fixed level, the control CPU 602 in the temperature control unit 601 controls the temperature of the air so that a deviation from a temperature range, which is set in advance by detecting temperature changes, is eliminated.

Upon the startup of the temperature control unit 601, the control CPU in the temperature control unit begins to flow air at the initial temperature that is set in advance, and adjusts the temperature of the air while checking feedback from the temperature measuring instruments 603.

That is, in step 1003, the control CPU 602 determines whether the measured temperature t is within a prescribed temperature range (more than $t_0 \times \Delta t_0$ but less than $t_0 + \Delta t_0$). If the temperature t falls within the prescribed temperature, the sequence proceeds to step 1004, in which the temperature of the temperature control medium is set to $t_0 + \Delta t_1$ and the sequence returns to step 1002.

If the measured temperature t is not within the prescribed range in step 1003, the sequence proceeds to step 1005, in which it is determined whether $t_0 + (t_0 - t)$ is within the range of temperatures controllable by the temperature control unit 601.

If $t_0 + (t_0 - t)$ is within the range of temperatures controllable by the temperature control unit 601, the sequence proceeds to step 1006, in which the temperature of the temperature control medium is set to $t_0 + (t_0 - t)$ and the sequence returns to step 1002.

If $t_0 + (t_0 - t)$ is not within the range of temperatures controllable by the temperature control unit 601 in step 1005, the sequence proceeds to step 1007, in which the temperature of the temperature control medium is set to a control temperature limit lower than $t_0 + (t_0 - t)$ and the sequence returns to step 1002.

Ideally, the temperature gradient is $t_0 + \Delta t_1$ in the outward pipe 611, $t_0$ in the temperature measuring instruments 603, and $t_0 + t_2$ in the inward pipe 612.

As described above, the air has a temperature gradient along the airflow 613. Accordingly, the longer a physical distance from the temperature measuring instruments 603 along the airflow 613 is, the lower the temperature stability is.

The temperature measuring instruments 603 are thus preferably disposed near its target that needs temperature control; for example, it is preferably grounded.

Furthermore, temperature characteristics, such as the amount of response displacement and response speed, should be considered for temperature variations of each target that needs temperature control.

In the first embodiment, temperature variations of the stone surface plate 501 are largest, followed by the optical surface plate 502 and other parts (the auto focus unit 210 and objective lens 201) in that order, and the response speed is reduced in that order.

As the response speed is increased, more unstable temperatures are followed. As the response speed is decreased, a result of a more averaged unstable temperature appears as variations, so the effect is small.

Accordingly, in the first embodiment, a position at which to dispose the temperature measuring instruments 603 was set to a mountable position at which the sum of the distance from the objective lens 201 and the distance from the auto focus unit 210 is minimized.

As described above, in the first embodiment of the present invention, the parts constituting the defect inspection apparatus are classified into parts that need temperature control and parts that do not need temperature control; all the parts that need temperature control are accommodated together into the temperature-controlled part accommodating section 604 so that a fixed temperature is kept.

Therefore, it becomes easy to keep a fixed temperature, when compared with a case in which individual parts are temperature-controlled separately by being heated or cooled, yielding an energy saving effect.

When compared with the case in which individual parts are temperature-controlled separately by being heated or cooled, it suffices to perform temperature control in a collective manner, reducing required temperature detecting devices and simplifying temperature control.

In addition, there is no need to cover the entire defect inspection apparatus, so it is not enlarged.

When the parts that need temperature control undergo temperature control in a collective manner as in the first embodiment of the present invention, it become possible to reduce footprints by about 10% to 20%, when compared with a case in which the entire apparatus is covered with a temperature control chamber.

A heat insulating material may be used to thermally isolate all the parts together that need temperature control from the ambient environment.

Second Embodiment

A second embodiment of the present invention will be described with reference to FIG. 8.

In the second embodiment of the present invention, a liquid is used as the temperature control medium, the height of the apparatus is reduced so that the FFU can be mounted, and inspection sensitivity is improved by eliminating optical path fluctuations by the use of airflows in the illumination optical system 100 and inspection optical system 200.

The basic structure is the same as in the first embodiment; that is, the parts constituting the defect inspection apparatus are classified into parts that need temperature control and parts that do not need temperature control, and the parts that need temperature control are kept at a fixed temperature in a collective manner.

Identical parts are therefore indicated by identical reference numerals, and only descriptions that differ between the first and second embodiments will be given below.

Figure 8:
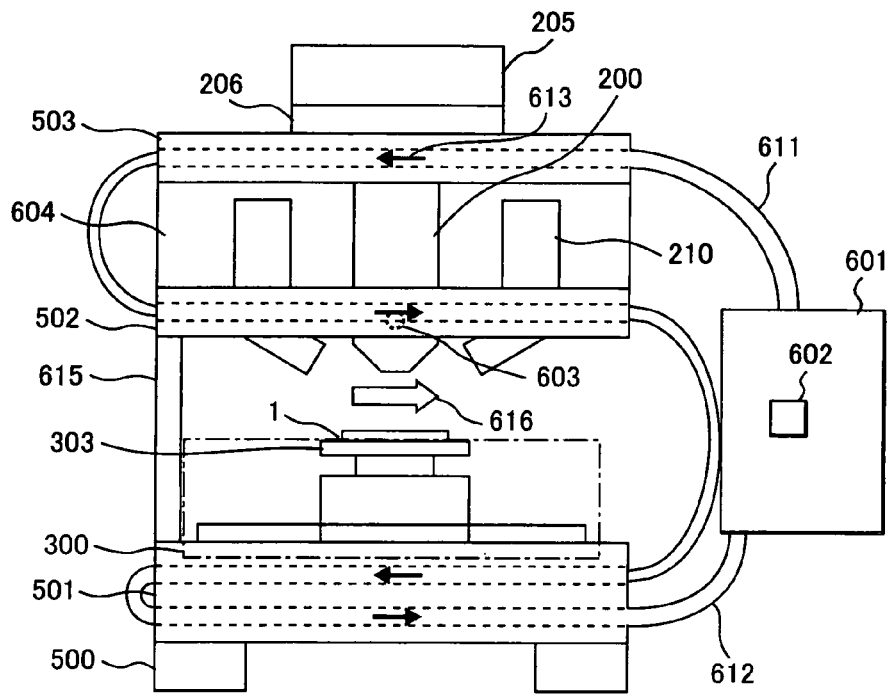
FIG. 8 is a drawing to show a schematic structure of the temperature control system in a second embodiment of the present invention.

On the optical surface plate 502 in FIG. 8, the illumination optical system 100, at least one set of the inspection optical system 200, the auto focus unit 210, and a second optical surface plate 503 are mounted.

The stone surface plate 501 and the like are supported by bases 500. To simplify the drawing, columns for supporting the optical surface plate 502 from the stone surface plate 501 are omitted.

The sensor Z driving mechanism 206 and detector 205 are mounted on the second optical surface plate 503.

The range accommodated by the temperature-controlled part accommodating section 604 is from the lower end of the optical surface plate 502 to the upper end of the second optical surface plate 503.

In a broad sense, the stone surface plate 501 can also be included in the temperature-controlled part accommodating section 604. Other members are included in the heat radiating unit 605.

The interior of the temperature-controlled part accommodating section 604 is monitored by the temperature measuring instruments 603. Obtained temperature data is loaded in a control CPU 602 in the temperature control unit 601 through a communication cable.

To keep the temperature in the apparatus at a fixed level, the control CPU 602 in the temperature control unit 601 controls the temperature of the temperature control liquid so that a deviation from a temperature range, which is set in advance by detecting temperature changes, is eliminated.

This liquid circulates along the flow path 613; the liquid passes through the temperature control unit 601, outward pipe 611, temperature-controlled part accommodating section 604, and inward pipe 612, and returns to the temperature control unit 601.

The liquid used for this temperature control is preferably, for example, pure water, fluorine-based inert liquid, hydro fluoro ether (HFE), ethylene glycol, or another substance that does not corrode the members included along the flow path 613.

The temperature control liquid directly performs temperature control on the stone surface plate 501, optical surface plate 502, and the second optical surface plate 503. The surface plates, the temperatures of which are directly controlled, function as indirect temperature control units and control the temperature in the temperature-controlled part accommodating section 604.

In the example shown in FIG. 8, a set of the temperature measuring instrument 603 and temperature control unit 601 performs temperature control.

In this case, a device is preferably made for a place at which to mount the temperature measuring instrument 603, as described later.

A plurality of sets of temperature control units 601, control CPUs 602 in temperature control units, and temperature measuring instruments 603 may be used to perform temperature control separately for the stone surface plate 501, optical surface plate 502, and second optical surface plate 503.

In this case, the temperature measuring instruments 603 are preferably disposed near the center of the flow path 613 of each surface plate.

The temperature control liquid in the second embodiment of the present invention lacks an air cleaning function as used in the first embodiment.

Accordingly, the FFU 615 is preferably disposed in such a way that clean air along an airflow 616 between the stone surface plate 501 and optical surface plate 502 blows dust near the surface of the wafer 1 off the apparatus.

If the clean air is directed in the direction of the airflow 616 (from left to right in FIG. 8), rather than downwardly, the FFU 615 may be disposed next to the apparatus, enabling the height of the apparatus to be reduced.

In the second embodiment of the present invention, it becomes easy to keep a fixed temperature, when compared with a case in which individual parts are temperature-controlled separately by being heated or cooled, yielding an energy saving effect, as in the first embodiment.

In the second embodiment of the present invention, there is no airflow in the temperature-controlled part accommodating section 604, so optical path fluctuations in the illumination optical system 100 and inspection optical system 200 can be significantly reduced, improving the sensitivity stability.

A position at which to dispose the temperature measuring instruments 603 in the second embodiment of the present invention is preferably set to a position within the optical surface plate 502 at which the sum of the distance from the objective lens 201 and the distance from the auto focus unit 210 is minimized.

This is because if the temperature measuring instruments 603 are disposed at the same position as in the first embodiment, an ambient temperature is measured.

In FIG. 8, part of the objective lens 201 and auto focus unit 210 touches the airflow 616, but only their ends are brought into contact and most parts are temperature-controlled by internal thermal conduction.

In the second embodiment of the present invention, temperature is indirectly controlled, so the temperature controlled in the temperature-controlled part accommodating section 604 is more stable than in the first embodiment. However, the temperature in the temperature-controlled part accommodating section 604 responds slowly to temperature control by the temperature control unit 601.

Consequently, variations in ambient temperature are highly likely to affect the temperature-controlled part accommodating section 604 through side walls.

For these reasons, a heat insulating material is preferably used for the side walls of the temperature-controlled part accommodating section 604.

The flow path 613 is preferably arranged near its upper surface of the second optical surface plate 503.

The reason for this arrangement is to prevent a temperature gradient from occurring in the second optical surface plate 503 due to the effect of the outside air and temperature variations of the detector 205.

For a similar reason, in the first optical surface plate 502, the flow path 613 is disposed near its lower surface; in the stone surface plate 501, the flow path 613 is disposed near its upper and lower surfaces as much as possible.

In this embodiment, each surface plate is holed so as to form the airflow. A temperature-controlled sheet may be attached to each surface plate instead of making holes so as to perform temperature control.

It is also possible to use both a holed surface plate and a surface plate to which a sheet is attached.

Third Embodiment

A third embodiment of the present invention will be described with reference to FIG. 9.

In the third embodiment of the present invention, in addition to the temperature control unit 601, heat sources in the apparatus are used for temperature control, reducing burdens on the apparatus manufacturing line and semiconductor line caused by energy.

The basic structure is the same as in the first embodiment; that is, the parts constituting the defect inspection apparatus are classified into parts that need temperature control and parts that do not need temperature control, and the parts that need temperature control are kept at a fixed temperature in a collective manner.

Only descriptions that differ between the first and third embodiments will be given below.

Figure 9:
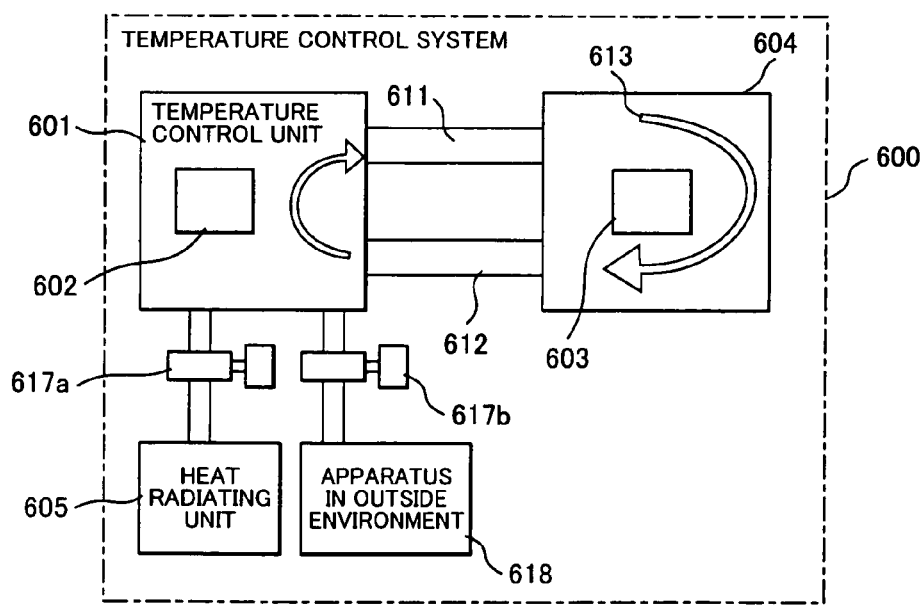
FIG. 9 is a drawing to show a schematic structure of the temperature control system in a third embodiment of the present invention.

In FIG. 9, the temperature control unit 601 is connected to the heat radiating unit 605 (first heat radiating unit) via a pipe that is provided with a heat insulating valve 617a. The temperature control unit 601 is also connected to an apparatus 618 (second heat radiating unit) in the outside environment via another pipe that is provided with a heat insulating valve 617b.

The temperature control unit 601 does not control the temperature of a medium by using only electric power; the control CPU 602 in the temperature control unit 601 adjusts the heat insulating valves 617a and 617b and heat from the heat radiating unit 605 and apparatus in the outside environment are used to control the temperature of the medium.

That is, a second temperature measuring unit measures the temperature of the heat radiating unit 605, and a third temperature measuring unit measures the temperature of the apparatus 618 in the outside environment; when the temperature in the temperature-controlled part accommodating section 604 controlled to be at a constant temperature, either the heat radiating unit 605 or the apparatus 618 in the outside environment is determined to be suitable for heat exchange, and the operation of opening and closing the insulating valves 617a and 617b is controlled so that the heat exchanging medium can be circulated.

This arrangement can not only reduce electric power consumed by the temperature control unit 601 but also can reduce heat radiated from the temperature control unit 601 and heat radiating unit 605, improving the energy efficiency of the apparatus manufacturing line and semiconductor line.

In a variation of the third embodiment, a plurality of parts and regions in the heat radiating unit 605 in the inspection apparatus are classified into parts and regions with high generated heat temperatures and parts and regions with low generated heat temperatures and accommodated in a high-temperature part accommodating section and a low-temperature part accommodating section, each of which is equipped with a temperature measuring unit and also provided with pipes and valves to connect with the temperature control unit 601, and determines which section to be exchanged a heat according to the measured temperature.

In this arrangement, parts and regions that do not need temperature control can be used to fix the temperatures of parts that need temperature control, enabling the temperatures to be controlled more efficiently, that is, with less energy consumption.

In this variation, the apparatus 618 in the outside environment may be used for heat exchange, and an arrangement in which the apparatus 618 in the outside environment is not used for heat exchange may be formed.

Although the above embodiments have been described by using a defect inspection apparatus that uses laser light to detect wafer defects, such as foreign matter, dirt, cracks, crystal defects, COPs, and pattern defects, as an example, the present invention can be applied to not only apparatuses that use laser light to inspect foreign matter on the wafer but also defect inspection apparatuses that use other types of light.

Specifically, some optical systems use not only laser light but also halogen lamps, mercury vapor lamps, Xe lamps, etc., and other optical systems are electronic optical systems that use electronic beams. The present invention can also be applied to defect inspection apparatuses using these optical systems.

Test objects are applied not only to wafers used as semiconductor substrates but also to glass substrates used in flat panel display units, ALTIC substrates, sapphire substrates used in sensors and LEDs, disk substrates, etc.

The present invention can be applied to a wide range of inspection apparatuses intended for surface inspection, mask inspection, bevel inspection, etc.

The temperature control according to the present invention can be performed by using heating due to a heater as well as electronic refrigeration and heating utilizing the Peltier effect or Seebeck effect.

Fourth Embodiment

In this embodiment described below, the focus position changes according to, for example, the weather conditions including atmospheric pressure and temperature.

This embodiment relates to an inspection apparatus that checks for foreign matte, defects, and the like on a semiconductor wafer etc. in, for example, a semiconductor manufacturing process.

To increase a yield in a semiconductor manufacturing process by minimizing failures, it is usually important to detect foreign matter and defects on wafers in the process with high sensitivity, classify detected results, determine causes, and take action accordingly.

An inspection apparatus (referred to below as the foreign matter inspection apparatus) is used to detect and classify these foreign matters and defects. High sensitivity, high throughput, and high classification performance are demanded for the foreign matter inspection apparatus.

The following documents relates to this type of foreign matter inspection apparatus.

Japanese Patent Application Laid-open Publication No. Sho 62(1987)-89336

Japanese Patent Application Laid-open Publication No. Hei 1(1989)-117024

Japanese Patent Application Laid-open Publication No. Hei 1(1989)-250847

Japanese Patent Application Laid-open Publication No. Hei 6(1994)-258239

Japanese Patent Application Laid-open Publication No. Hei 6(1994)-324003

Japanese Patent Application Laid-open Publication No. Hei 8(1996)-210989

Japanese Patent Application Laid-open Publication No. Hei 8(1996)-271437

Japanese Patent Application Laid-open Publication No. 2000-105203

The foreign matter inspection apparatuses disclosed in these documents perform focus adjustment in order to obtain high sensitivity.

The focus position changes according to the weather conditions including atmospheric pressure and temperature.

Specifically, changes in atmospheric pressure and temperature each cause a change in air density, changing the index of refraction of air and then changing the focus position.

Noting that changes in atmospheric pressure and temperature cause a change in focal position in an optical system, this embodiment was devised in the course of taking action against sensitivity variations involved in the weather conditions.

As described above, an apparatus including an optical system usually needs focus adjustment to obtain an optimum image.

With an exposing apparatus such as a stepper or scanner, the quality of an image can be directly monitored through a through-the-lens (TTL); even if a focus change occurs in the exposure optical system due to an atmospheric pressure and temperature, the focus can be adjusted by monitoring the image quality and thereby the focus changed by the atmospheric pressure and temperature can also be adjusted.

This arrangement is applied not only to an exposing apparatus but also to general apparatuses that can directly monitor image quality through an optical system, such as for example a camera.

However, the foreign matter inspection apparatus cannot adjust the focus by a method in which image quality is directly monitored through a microscopic optical system.

To solve this problem, a focus control optical system is provided in addition to the microscopic optical system intended for foreign matter inspection.

To achieve focus adjustment by a detection optical system in the foreign matter inspection apparatus, a Z coordinate at which signal intensity is maximized, which is a performance index of the apparatus, is found by the microscopic optical system in advance; a focus control optical system then performs control so that the Z coordinate is maintained.

An operation for searching for the Z coordinate at which the signal intensity is maximized is a calibration operation rather than an operation specific to the foreign matter inspection apparatus. Although it is necessary that the Z coordinate is frequently searched for so as to suppress the effect by focus variations to a minor level, this operation is complicated and drops the availability of the apparatus.

As described above, the focus adjustment in the foreign matter inspection apparatus involves problems described below.

A functional problem in the focus adjustment is that the optimum Z coordinate at which the signal intensity is maximized varies with changes in weather conditions including atmospheric pressure and temperature, reducing the sensitivity.

A problem with a focus adjustment task is that the task is complicated and takes much time (three to eight minutes).

To suppress the effect by focus variations to a minor level, the focus adjustment task needs to be performed frequently at time intervals shorter than time intervals at which the atmospheric pressure and temperature change.

According to measurements, the atmospheric pressure and temperature may change at time intervals of about two hours. To avoid an effect by this change, the focus adjustment operation must be performed about once per hour.

This embodiment addresses this problem with an object of always maintaining a maximum sensitivity and eliminating the focus adjustment task that would otherwise need to be performed to maintain high sensitivity.

Another object of this embodiment is to improve the availability of the apparatus by eliminating the focus adjustment task that would otherwise reduce the availability.

A first feature of this embodiment to achieve the above objects is that attention has been focused on that a Z coordinate is changed by changes in atmospheric pressure and temperature, as described below.

First, according to the equation of state of a gas, "PV=nRT" holds.

(P=pressure [atm], V: volume (L), n: number of moles, R: gas constant (=0.082), T: absolute temperature [K])

Let n be w/M (w: mass, M: molecular weight) and V be w/d (d: density [g/L]), then the equation of state of a gas can be rewritten as "d=PM/TR" and further as "Δd=ΔPM/ΔTR".

This unit that a change in air density is proportional to a change in atmospheric pressure and inversely proportional to a change in temperature.

According to the Gladstone-Dale equation, "N=1+d·r" then holds.

(N: index of refraction, d=density [g/L], r=Gladstone-Dale constant)

This unit that a change in air density is proportional to a change in index of refraction in an optical system.

According to the Snell's law, a change in index of refraction finally becomes a change in focal length (Z coordinate).

A second feature of this embodiment is that since an atmospheric pressure sensor and a temperature sensor are provided, a change in focus due to a weather condition change can be comprehensively compensated for.

If, for example, only an atmospheric sensor or temperature sensor is used for compensation, it cannot be said that a change in focus due to weather condition changes is comprehensively compensated for.

However, it would be understood that, in an environment in which either the atmospheric pressure or temperature is controlled, it suffices to provide for compensation for a non-controlled parameter.

A third feature of this embodiment is that, in addition to stabilizing a Z coordinate by compensating for changes in atmospheric pressure and temperature, the Z coordinate continue to be compensated so that the maximum sensitivity is always obtained.

The method for this is achieved by the following simple control. An optimum Z coordinate at which the signal intensity is maximized is searched for in advance, and the atmospheric pressure, temperature, and optimum Z coordinate at that time (respectively referred to as the reference atmospheric pressure, reference temperature, and reference Z value) are used as three reference values; an atmospheric pressure and temperature are measured at an arbitrary point of time at which to detect foreign matter; differences from the reference values are taken and converted to a Z coordinate, and the converted Z coordinate is added to the reference Z value.

This embodiment is not limited to the foreign matter inspection apparatus, but efficiently effected to maintain the maximum signal intensity without performing the complicated focus adjustment operation in comprehensive apparatuses in which a focus adjustment operation cannot be performed by a method of directly monitoring image quality and a microscopic optical system and a focus control optical system are provided.

According to this embodiment described above, it suffices to search for an optimum Z coordinate once, after which the Z coordinate can be controlled while variations in atmospheric pressure and temperature are being monitored. Even apparatuses that cannot directly monitor image quality, such as the foreign matter inspection apparatus, can perform inspection with the signal intensity always kept at the maximum level.

According to this embodiment, the complicated focus adjustment task that would otherwise need to be performed about once per hour in three to eight minutes is eliminated, improving the availability of the apparatus.

This embodiment relates to focus adjustment in a foreign matter inspection apparatus that has the features described above and inspects foreign matter on a wafer.

FIG. 1 is a drawing to show the schematic structure of the foreign matter inspection apparatus of this embodiment.

Figure 10:
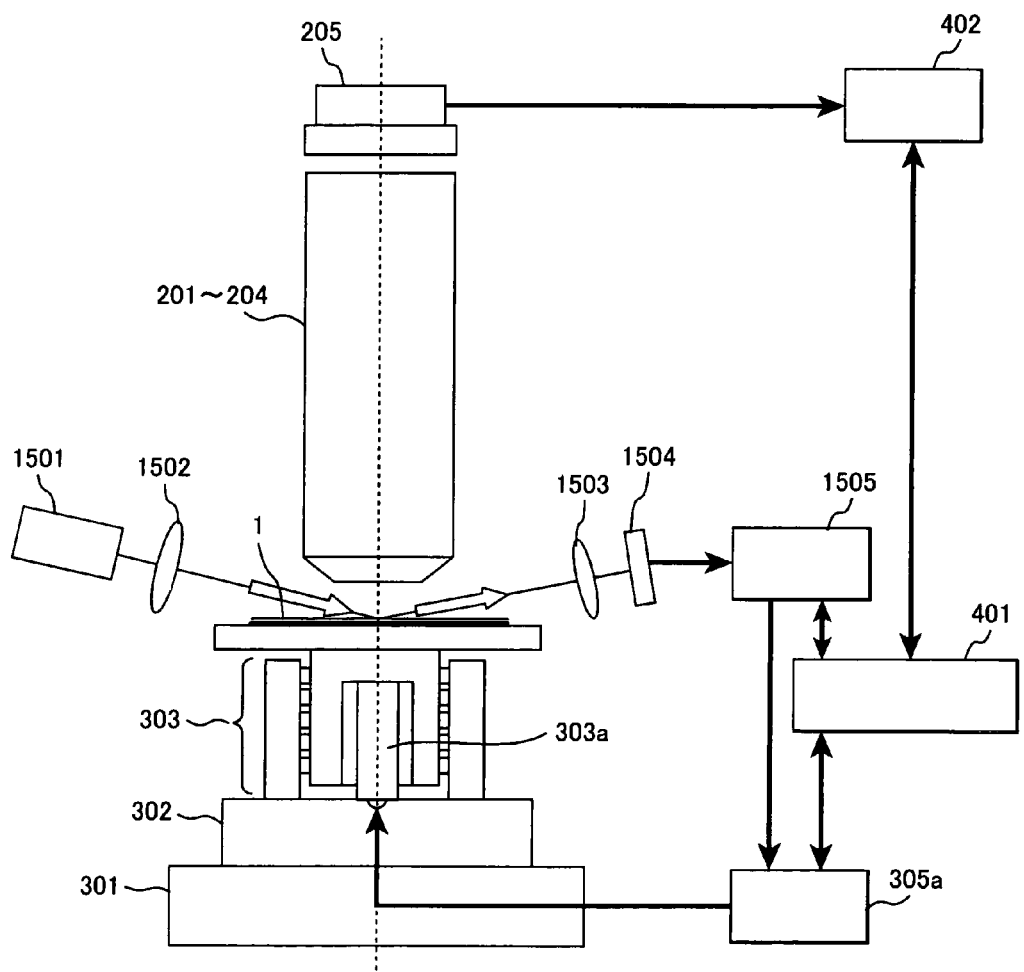
FIG. 10 is a drawing to show the schematic structures of the foreign matter detection optical system and focus detection optical system of the foreign matter inspection apparatus.

FIG. 10 is a drawing to show the schematic structure of the foreign matter detection optical system and the structure of the focus detection optical system of the foreign matter inspection apparatus.

Figure 11:
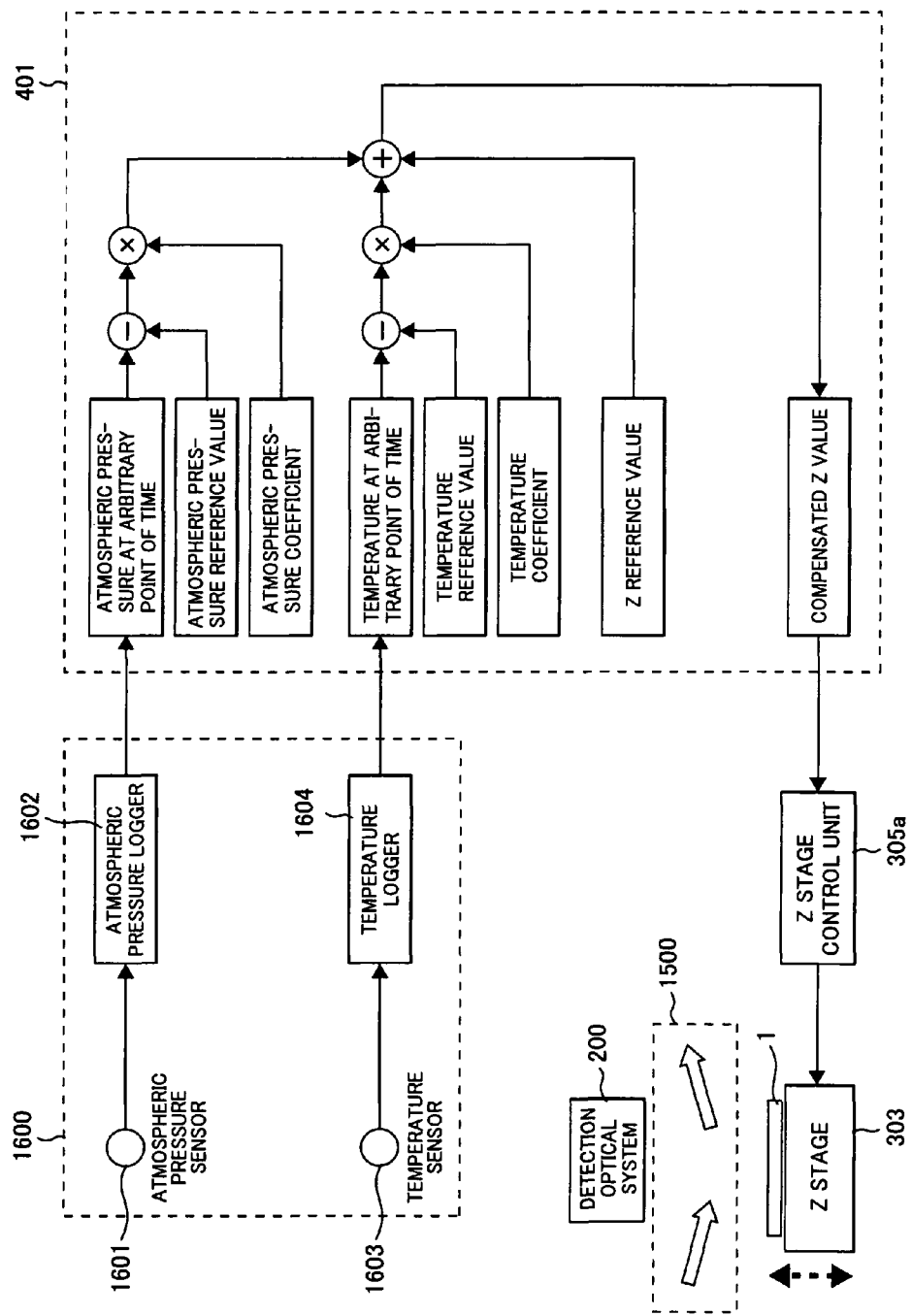
FIG. 11 is a block diagram of an embodiment for compensating for an atmospheric pressure and temperature.

FIG. 11 is a block diagram of an embodiment for compensating for an atmospheric pressure and temperature.

The embodiment of the foreign matter inspection apparatus comprises a stage unit 300 having an X stage 301, Y stage 302, Z stage 303, and θ stage 304 on which a wafer 1 to be inspected is mounted as well as a stage controller 305, a illumination optical system 100 having a laser light source 101 etc., illumination beam spot imaging units 110, 120, and 130, an foreign matter inspection optical system 200 having a objective lens 201, spatial filter 202, imaging lens 203, varifocal lens group 204, and a one-dimensional detector (image sensor) 205 such as a TDI sensor, and a control system 400 having a signal processing system 402, an output unit for storing defect detection results such as for foreign matter and delivering the defect detection results, a calculation processing system 401 for controlling the driving of a motor etc., coordinates, and sensors, a display system 403, and an input system 404.

Other reference numerals are indicating as followings. 1500: focus detection optical system, 1501: focus detection light source, 1502: focus detection phototransmitting optical system, 1503: photoreceiving optical system, 1504: focus detection sensor, 1505: focus signal processing unit, 1600: atmospheric pressure and temperature sensor system, 1601: atmospheric pressure sensor, 1602: atmospheric pressure data logger, 1603: temperature sensor, 1604: temperature data logger.

The three illumination beam spot imaging units 110, 120, and 130 are structured so that lights emitted from the laser light source 101 illuminate the wafer 1 to be inspected from three directions.

The inspection optical system 200 is structured so that light produced from the wafer 1 is detected by a detection lens (objective lens) 201, the spatial filter 202 that shields a Fourier transformed image due to reflected and diffracted light from a repetition pattern, the imaging lens 203, and the one-dimensional detector 205 such as a TDI sensor.

For a stage operation during inspection, the X stage 301 and Y stage 302 are driven to perform illumination scanning on illumination beam spots over the entire surface of the wafer 1 under inspection.

For focus control during inspection, the focus detection optical system 1500 detects a position on the surface of the wafer 1 that is undergoing illumination scanning, and transfers a detected position signal to the focus signal processing unit 1505. The focus signal processing unit 1505 converts the position signal to the amount of movement of the Z driving apparatus 303a and transfers the converted signal to the Z stage control unit 305a.

The Z stage control unit 305a then drives the Z driving apparatus 303a, and the Z stage 303 moves up and down so that a fixed distance is maintained between the objective lens 201 and the surface of the wafer 1.

The distance between the objective lens 201 and the surface of the wafer 1 can be arbitrarily controlled by setting an offset in the Z stage control unit 305a.

In this embodiment, focus variations caused by changes in atmospheric pressure and temperature are controlled as offsets given to the Z stage control unit 305a.

Next, a procedure for compensating for focus variations in this embodiment will be explained.

At first, an example of temperature compensation will be used to explain a flow of compensation.

Figure 12:
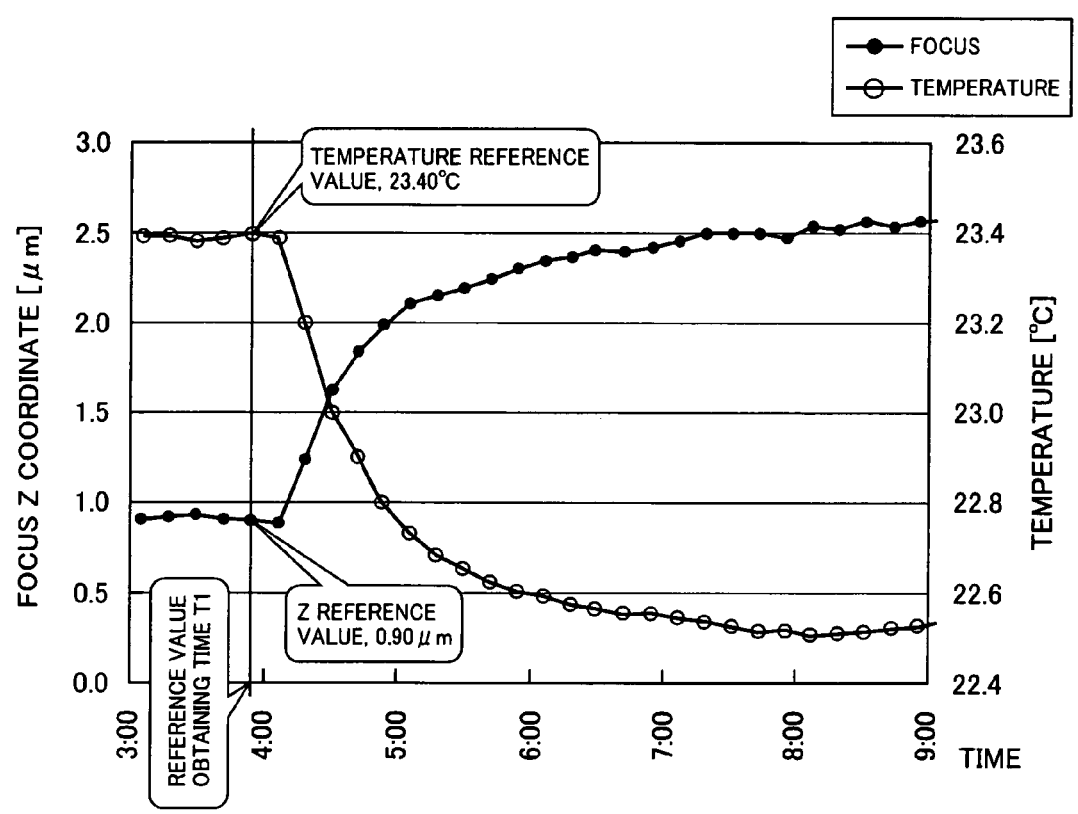
FIG. 12 is a graph to indicate temperature variations and changes in the focus Z coordinate under the condition where temperature is not compensated.

FIG. 12 is a graph to indicate temperature variations and changes in the focus Z coordinate when temperature is not compensated.

The focus Z coordinate is the Z coordinate at which the signal intensity is maximized, which is obtained by the focus adjustment task.

The temperature was changed step by step by a temperature controlled bath. The atmospheric pressure is constant.

Accordingly, FIG. 12 was obtained by performing the focus adjustment task repeatedly at different temperatures.

Figure 13:
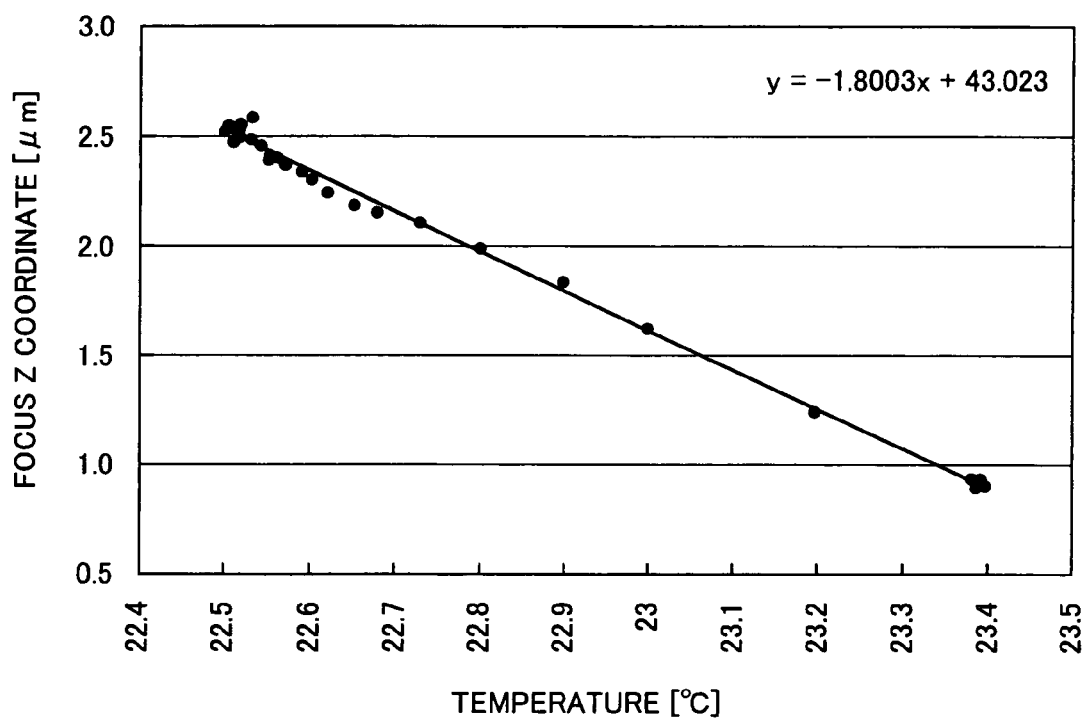
FIG. 13 is a graph to indicate the relation between the temperature and the focus coordinate is linear.

FIG. 13 a graph to indicate the relation between the temperature and the focus Z coordinate.

The temperature and focus Z coordinate can be represented as a linear function. It can be seen that the focus Z coordinate changes by −1.80 μm each time the temperature changes by 1° C. This value is saved as a temperature coefficient.

The temperature coefficient takes various values for different optical system structures.

Figure 14:
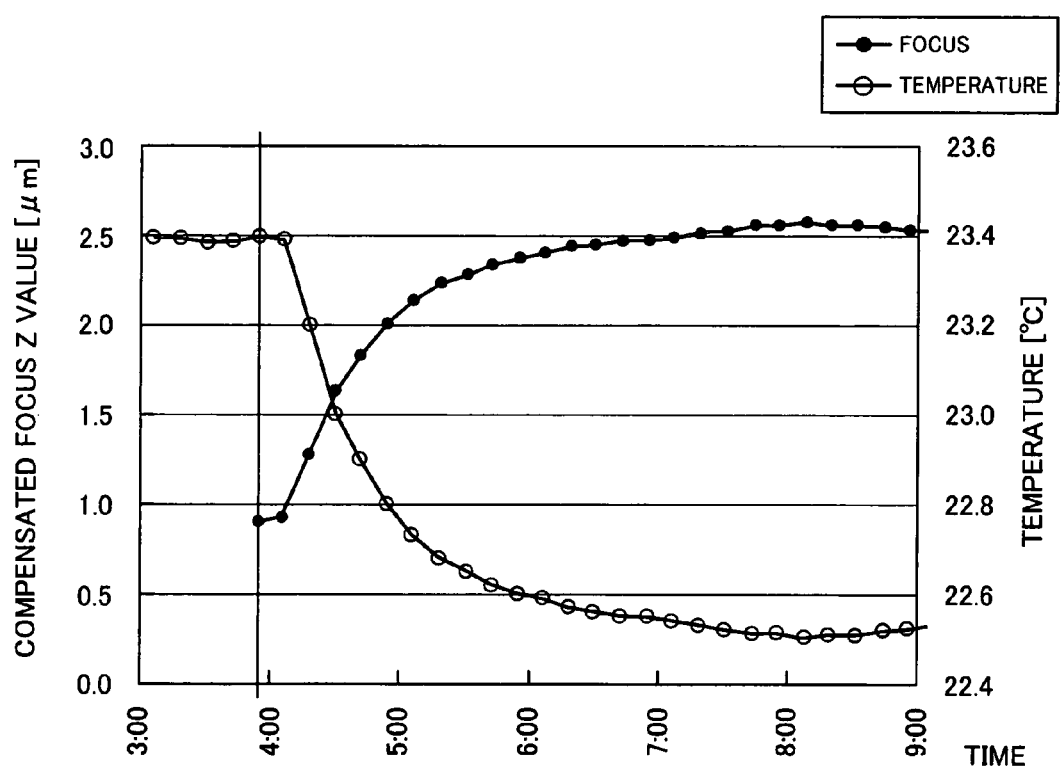
FIG. 14 is a graph to indicate temperature variations and Z compensated values for temperatures.

FIG. 14 is a graph to indicate temperature variations and Z compensated values for temperatures.

A Z compensated value for a temperature is obtained from the equation below.

Z compensated value for temperature=Z reference value+(temperature coefficient×(temperature reference value−temperature at arbitrary point of time))

That is, in the characteristics in FIG. 12, the Z reference value and temperature reference value were obtained at time T1; values after T1 were calculated as Z compensated values. That is, the focus Z coordinate value is obtained by calculation without having to performing the complicated focus adjustment task.

Figure 15:
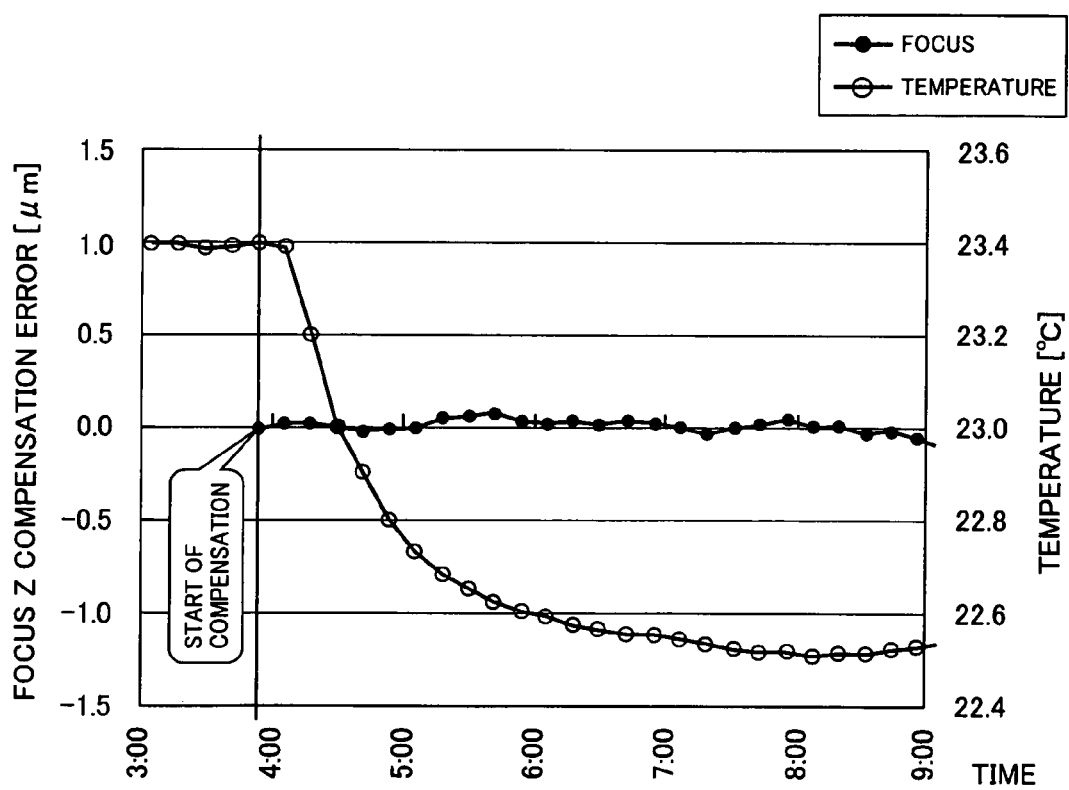
FIG. 15 is a graph obtained by subtracting the characteristics in FIG. 12 from the characteristics in FIG. 14. That is.

FIG. 15 a graph obtained by subtracting the characteristics in FIG. 12 from the characteristics in FIG. 14. That is, FIG. 15 indicates focus error in Z compensation for temperatures.

Remaining compensation error is caused due to deviation from the linear function between the temperature and the focus Z coordinate.

Focus error due to the Z compensation for temperatures is 0.1 μm or less, which is sufficiently small and is not problematic in practical use.

Next, an example of atmospheric pressure compensation will be used to explain a flow of compensation. A procedure for this compensation is the same as the procedure for temperature compensation.

Figure 16:
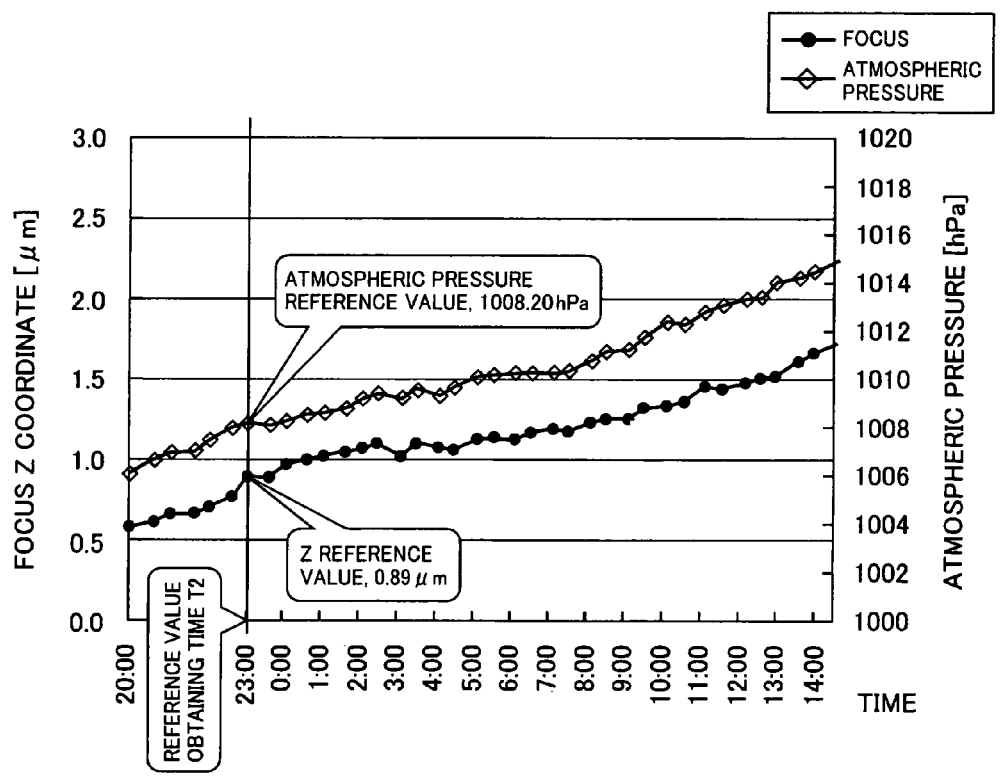
FIG. 16 is a graph to indicate atmospheric pressure variations and changes in the focus Z coordinate under the condition where atmospheric pressure is not compensated.

FIG. 16 a graph to indicate atmospheric pressure variations and changes in the focus Z coordinate when atmospheric pressure is not compensated.

Changes in atmospheric pressure were obtained as changes in weather. Temperature was kept constant in a temperature controlled bath.

Figure 17:
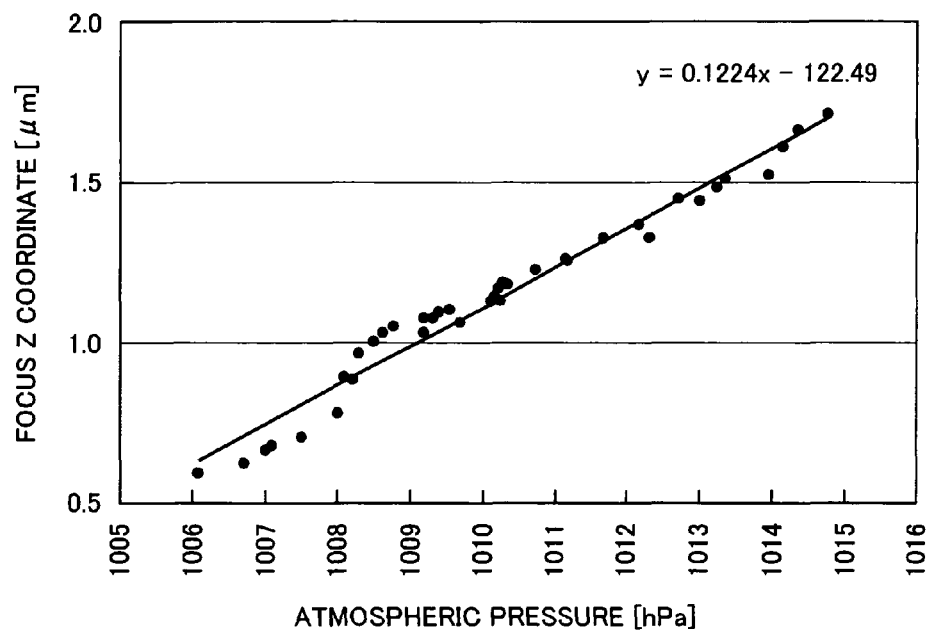
FIG. 17 is a graph to indicate the relation between the atmospheric pressure and the focus coordinate is linear.

FIG. 17 is a graph to indicate the relation between the atmospheric pressure and the focus Z coordinate.

The atmospheric pressure and focus Z coordinate can be represented as a linear function. It can be seen that the focus Z coordinate changes by +0.12 μm each time the atmospheric pressure changes by 1 hPa. This value is saved as an atmospheric pressure coefficient.

The atmospheric pressure coefficient also takes various values for different optical system structures.

Figure 18:
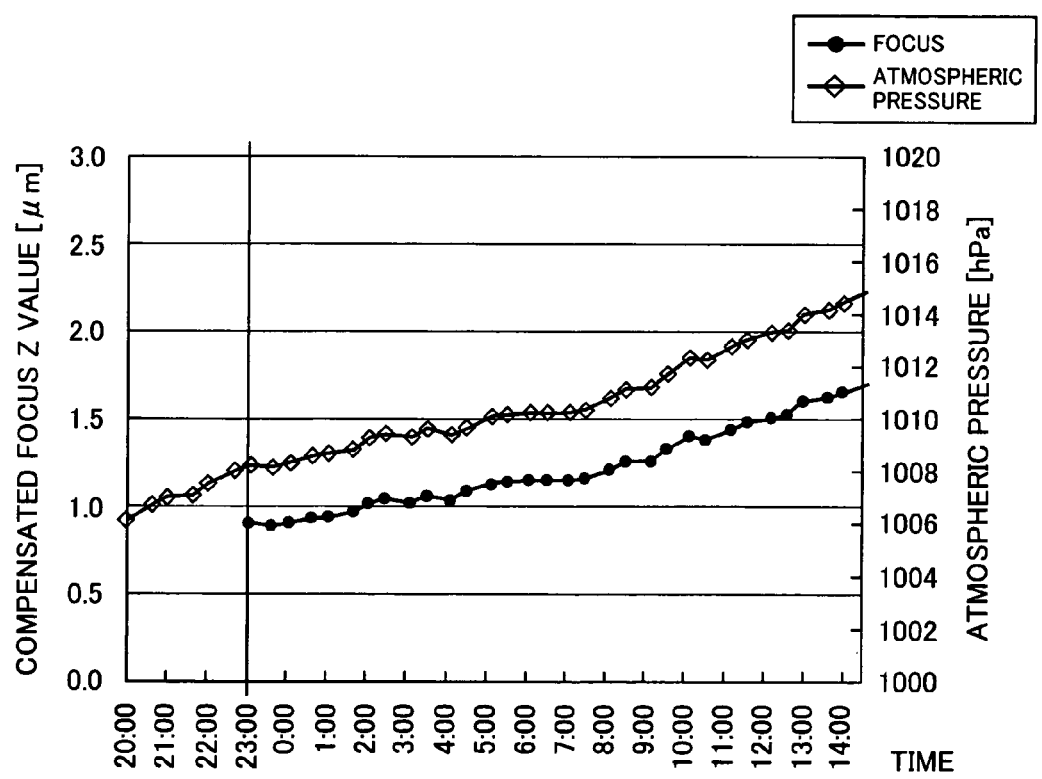
FIG. 18 is a graph to indicate atmospheric pressure variations and Z compensated values.

FIG. 18 is a graph to indicate atmospheric pressure variations and Z compensated values for atmospheric pressures.

A Z compensated value for an atmospheric pressure is obtained from the equation below.

Z compensated value for atmospheric pressure=Z reference value+(atmospheric pressure coefficient×(atmospheric pressure reference value−atmospheric pressure at arbitrary point of time))

That is, in the characteristics in FIG. 16, the Z reference value and atmospheric pressure reference values were obtained at time T2; values after T2 were calculated as Z compensated values.

Figure 19:
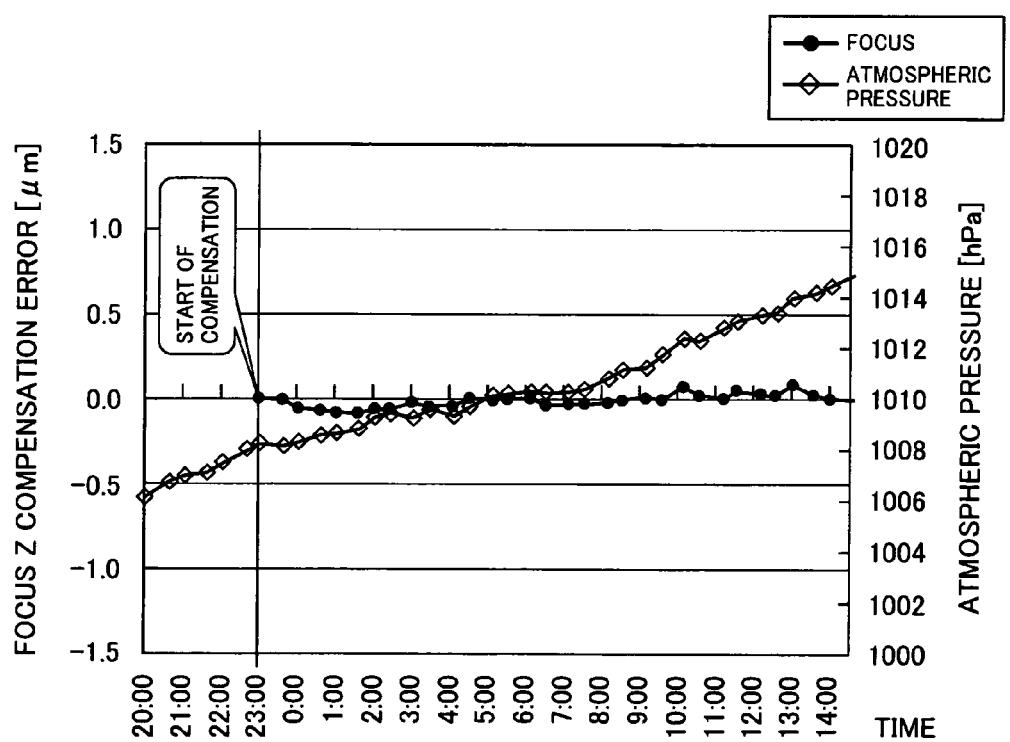
FIG. 19 is a graph obtained by subtracting the characteristics in FIG. 16 from the characteristics in FIG. 18. That is.

FIG. 19 is a graph obtained by subtracting the characteristics in FIG. 16 from the characteristics in FIG. 18. That is, FIG. 19 indicates focus error in Z compensation for atmospheric pressures.

Remaining compensation error is caused due to deviation from the linear function between the atmospheric pressure and the focus Z coordinate.

Focus error due to the Z compensation for atmospheric pressures is 0.1 μm or less, which is sufficiently small.

Next, an arrangement for compensation will be explained.

FIG. 11 is a block diagram of an embodiment for compensating for an atmospheric pressure and temperature.

An atmospheric pressure measured by the atmospheric pressure sensor 1601 at an arbitrary point of time is stored in the atmospheric pressure data logger 1602.

A temperature measured by the temperature sensor 1603 at an arbitrary point of time is stored in the temperature data logger 1604.

Stored in the control CPU 401 are a Z coordinate (Z reference value) at which a maximum sensitivity is obtained, an atmospheric pressure (atmospheric pressure reference value) at that point of time, a temperature (temperature reference value) at that point of time, the coefficient (atmospheric pressure coefficient), which is obtained in advance so as to convert atmospheric pressures to Z coordinates, and the coefficient (temperature coefficient), which is also obtained in advance so as to convert temperatures to Z coordinates.

In compensation for atmospheric pressure variations, a difference between an atmospheric pressure measured at an arbitrary point of time and the atmospheric pressure reference value is taken, the difference is multiplied by the atmospheric pressure coefficient to obtain a Z converted value for the difference, and the Z converted value for the atmospheric pressure is added to the Z reference value, yielding a Z compensated value.

In compensation for temperature variations, a difference between a temperature measured at an arbitrary point of time and the temperature reference value is taken, the difference is multiplied by the temperature coefficient to obtain a Z converted value for the difference, and the Z converted value for the temperature is added to the Z reference value, yielding a Z compensated value.

Compensation for atmospheric pressure variations and compensation for temperature variations are performed separately.

Accordingly, when a Z compensated value for an atmospheric pressure and another Z compensated value for a temperature are added to the Z reference value to obtain a Z compensated value, the atmospheric pressure and temperature can be compensated for at the same time.

The obtained Z compensated value is sent to the Z stage control unit 305a, and an offset is given to the focus following operation performed by the Z stage 303.

The offset given to the focus following operation provides the effect that variations in focus caused by changes in atmospheric pressure and temperature are corrected.

As described above, when control is performed, variations in focus caused by changes in atmospheric pressure and temperature are corrected.

The invention claimed is:

1. A defect inspection apparatus emits light to a test object, detects reflected or scattered light from the test object and detects a defect in the test object, comprising:
   a temperature-controlled part accommodating section for accommodating a plurality of parts that need temperature control, which is out of the plurality of parts in the defect inspection apparatus;
   a first temperature measuring instrument measures a temperature in the temperature-controlled part accommodating section;
   a temperature control unit controls the temperature of the interior of the temperature-controlled part accommodating section at a fixed level by controlling air temperature so that a deviation from a predetermined temperature range is eliminated;
   a first heat radiating unit for accommodating parts that do not need temperature control, which is out of the plurality of parts in the defect inspection apparatus;
   a second heat radiating unit performs heat exchange outside the defect inspection apparatus;
   a second temperature measuring instrument for measuring the temperature of the first heat radiating unit; and
   a third temperature measuring instrument for measuring the temperature of the second heat radiating unit,
   wherein the temperature control unit determines whether either the first heat radiating unit or the second heat radiating unit is used for heat exchange according to temperature measurement results obtained by the second temperature measuring instrument and the third temperature measuring instrument, and controls the temperature of the interior of the temperature-controlled part accommodating section at a prescribed temperature.

2. A defect inspection apparatus to inspect a surface of a test object comprising:
   a temperature-controlled part accommodating section for accommodating a plurality of parts that need temperature control, which is out of the plurality of parts in the defect inspection apparatus;
   a first temperature measuring instrument measures a temperature in the temperature-controlled part accommodating section;

a temperature control unit controls the temperature of the interior of the temperature-controlled part accommodating section at a fixed level by controlling air temperature so that a deviation from a predetermined temperature range is eliminated;

a first heat radiating unit for accommodating parts that do not need temperature control, which is out of the plurality of parts in the defect inspection apparatus;

a second heat radiating unit performs heat exchange outside the defect inspection apparatus;

a second temperature measuring instrument for measuring the temperature of the first heat radiating unit; and a third temperature measuring instrument for measuring the temperature of the second heat radiating unit, wherein the temperature control unit determines whether either the first heat radiating unit or the second heat radiating unit is used for heat exchange according to temperature measurement results obtained by the second temperature measuring instrument and the third temperature measuring instrument, and controls the temperature of the interior of the temperature-controlled part accommodating section at a prescribed temperature.

3. The defect inspection apparatus according to claim 1 or 2, wherein the defect inspection apparatus is an inspection apparatus for inspecting a surface of a wafer; the plurality of parts which need temperature control include an objective lens and an auto focus unit.

4. The defect inspection apparatus according to claim 1 or 2, wherein an airflow is circulated between the temperature-controlled part accommodating section and the temperature control unit and the temperature control unit controls the temperature in the temperature-controlled part accommodating section at the prescribed temperature.

5. The defect inspection apparatus according to claim 4, further comprising a clean filter for removing dust included in an airflow which is expelled from the temperature control unit and enters the temperature-controlled part accommodating section.

6. The defect inspection apparatus according to claim 1 or 2, wherein a liquid is circulated between the temperature-controlled part accommodating section and the temperature control unit and the temperature control unit controls the temperature in the temperature-controlled part accommodating section at the prescribed temperature.

7. The defect inspection apparatus according to claim 1 or 2, wherein the first temperature measuring instrument considers temperature characteristics selected from amount of response displacement and response speed.

8. The defect inspection apparatus according to claim 1 or 2, wherein a position of the temperature measuring instrument is set at a mountable position at which the sum of the distance from an objective lens and the distance from an auto focus unit is minimized.

9. The defect inspection apparatus according to claim 1 or 2, wherein the temperature-controlled part accommodating section is made of a heat insulating material.

10. A defect inspection apparatus emits light to a test object, detects reflected or scattered light from the test object and detects a defect in the test object, the apparatus comprising:

a temperature-controlled part accommodating section for accommodating a plurality of parts that need temperature control, which is out of the plurality of parts in the defect inspection apparatus;

a first temperature measuring instrument measures a temperature in the temperature-controlled part accommodating section;

a temperature control unit controls the temperature of the interior of the temperature-controlled part at a fixed level by controlling air temperature so that a deviation from a predetermined temperature range is eliminated;

a high-temperature part accommodating section for accommodating high-temperature parts, which is out of high-temperature parts that do not need temperature control in the defect inspection apparatus;

a low-temperature part accommodating section for accommodating low-temperature parts that do not need temperature control;

a second temperature measuring instrument for measuring a temperature in the high-temperature part accommodating section; and a third temperature measuring instrument for measuring a temperature in the low-temperature part accommodating section, wherein the temperature control unit determines whether either the high-temperature part accommodating section or the low-temperature part accommodating section is used for heat exchange according to temperature measurement results obtained by the second temperature measuring instrument and the third temperature measuring instrument, and controls the temperature of the interior of the temperature-controlled part accommodating section at a prescribed temperature.

11. A defect inspection apparatus to inspect a surface of a test object, the apparatus comprising:

a temperature-controlled part accommodating section for accommodating a plurality of parts that need temperature control, which is out of the plurality of parts in the defect inspection apparatus;

a first temperature measuring instrument measures a temperature in the temperature-controlled part accommodating section;

a temperature control unit controls the temperature of the interior of the temperature-controlled part accommodating section at a fixed level by controlling air temperature so that a deviation from a predetermined temperature range is eliminated;

a high-temperature part accommodating section for accommodating high-temperature parts, which is out of high-temperature parts that do not need temperature control in the defect inspection apparatus;

a low-temperature part accommodating section for accommodating low-temperature parts that do not need temperature control;

a second temperature measuring instrument for measuring a temperature in the high-temperature part accommodating section; and a third temperature measuring instrument for measuring a temperature in the low-temperature part accommodating section, wherein the temperature control unit determines whether either the high-temperature part accommodating section or the low-temperature part accommodating section is used for heat exchange according to temperature measurement results obtained by the second temperature measuring instrument and the third temperature measuring instrument, and controls the temperature of the interior of the temperature-controlled part accommodating section at a prescribed temperature.

* * * * *